United States Patent
McCollam et al.

(10) Patent No.: US 11,197,860 B2
(45) Date of Patent: Dec. 14, 2021

(54) TREATMENT OF PRIMARY BILIARY CHOLANGITIS AND PRIMARY SCLEROSING CHOLANGITIS WITH BARICITINIB

(71) Applicant: Eli Lilly and Company, Indianapolis, IN (US)

(72) Inventors: Patrick L McCollam, Greenwood, IN (US); James Michael McGill, Carmel, IN (US); Ana Luisa de Macedo Pinto Correia, Lisbon (PT)

(73) Assignee: Eli Lilly and Company, Indianapolis, IN (US)

( * ) Notice: Subject to any disclaimer, the term of this patent is extended or adjusted under 35 U.S.C. 154(b) by 59 days.

(21) Appl. No.: 16/598,241

(22) Filed: Oct. 10, 2019

(65) Prior Publication Data

US 2020/0121685 A1  Apr. 23, 2020

Related U.S. Application Data

(60) Provisional application No. 62/746,589, filed on Oct. 17, 2018.

(51) Int. Cl.
| | | |
|---|---|---|
| *A61P 1/16* | (2006.01) | |
| *A61K 31/519* | (2006.01) | |
| *A61K 9/00* | (2006.01) | |

(52) U.S. Cl.
CPC .......... *A61K 31/519* (2013.01); *A61K 9/0053* (2013.01); *A61P 1/16* (2018.01)

(58) Field of Classification Search
CPC ....................................................... A61P 1/16
See application file for complete search history.

(56) References Cited

U.S. PATENT DOCUMENTS

| | | | |
|---|---|---|---|
| 8,158,616 | B2 | 4/2012 | Rodgers et al. |
| 8,420,629 | B2 | 4/2013 | Rodgers et al. |
| 2016/0052930 | A1 | 2/2016 | Fensome et al. |
| 2018/0134713 | A1 | 5/2018 | Kobierski et al. |

FOREIGN PATENT DOCUMENTS

| | | |
|---|---|---|
| WO | 2017/144995 A1 | 8/2017 |

OTHER PUBLICATIONS

Gerussi et al. Annals o f Hepatology 19 p. 5-16 (Year: 2020).*
Patent Cooperation Treaty International Search Report pertaining to International Application No. PCT/US2019/055566; International Filing Date: Oct. 10, 2019, dated Jan. 20, 2020.
Patent Cooperation Treaty Written Opinion of the International Searching Authority pertaining to International Application No. PCT/US2019/055566; International Filing Date: Oct. 10, 2019, dated Jan. 20, 2020.
Shi Jack G et al.: "The Pharmacokinetics, Pharmacodynamics, and Safety of Baricitinib, an Oral JAK 1/;2 Inhibitor, in Healthy Volunteers", Journal of Clinical Pharmacology, Lippincott CO, Hagerstown, MD, US, vol. 54, No. 12, 30 Nov. 30, 2014, pp. 1354-1361, XPOO9517969, ISSN: 0091-2700, DOI: 10.1002/JCPH. 354, Retrieved from the Internet: URL:http://onlinelibrary.wiley.com/journal/;10.1002/(ISSN)10.1002(ISSN)1552-4604, p. 1354.
FDA, Olumiant US Label, May 31, 2018.
Fridman JS, et al.,"Selective inhibition of JAK1 and JAK2 is efficacious in rodent models of arthritis preclinical characterization of INCB028050," *J Immunol.* 2010; 184(9):5298-5307.
O'Shea et al., "The JAK-STAT pathway: impact on human disease and therapeutic intervention," *Annu Rev Med.* 2015;66:311-28.
O'Shea et al., "JAKs and STATs in immunity, immunodeficiency, and cancer," *N Engl J Med. Review* Jan. 10, 2013;368(2);161-70.
Webb et al., "The immunogenetics of primary biliary cirrhosis: A comprehensive review," *J Autoimmun.* 2015;64:42-52.
Hirschfield et al., "The British Society of Gastroenterology/UK-PBC primary biliary cholangitis treatment and management guidelines," *Gut.* Mar. 28, 2018.[Epub ahead of print] (hereinafter "Hirschfield 2018").
G.M. Hirschfield, M.E. Gershwin, "The immunobiology and pathophysiology of primary biliary cirrhosis," *Annu. Rev. Pathol. Mech. Dis.* 8(1) (2013), pp. 303-330.
Nevens et al., POISE Study Group, "A Placebo-Controlled Trial of obeticholic Acid in Primary Bihary Cholangitis," *N Engl J Med.* Aug. 18, 2016;375(7):631-43.
Jessica K Dyson, et al., "Primaiy sclerosing cholangitis" *Lancet* 2018, 391: 2547-59.
Lunder AK, et al., "Prevalence of Sclerosing Cholangitis Detected by Magnetic Resonance Cholangiography in Patients With Long-term Inflammatory Bowel Disease," *Gastroenterology* 2016; 151:660-669.
Stiehl A, et al., "Development of dominant bile duct stenoses inpatients with primary sclerosing cholangitis treated with ursodeoxycholic acid: outcome after endoscopic treatment," *J Hepatol.,* 36: 151-156, 2002.

(Continued)

*Primary Examiner* — Emily A Bernhardt
(74) *Attorney, Agent, or Firm* — Kyle W. Grimshaw

(57) ABSTRACT

Methods of treating Primary Biliary Cholangitis and/or Primary Sclerosing Cholangitis with baricitinib, including formulations and dose regimens. The amount of baricitinib may be administered as a 4 mg tablet or pill that includes one or more excipients. The amount of baricitinib may be administered daily or at some other frequency.

20 Claims, No Drawings

(56) References Cited

OTHER PUBLICATIONS

Webster K. et al., "The Functional Assessment of Chronic Illness Therapy (FACIT) measurement system: properties, applications, and interpretation," *Health and Quality of Life Outcomes* 2003;1:79.

Jacoby A., et al., "Development, validation, and evaluation of the PBC-40, a disease specific health related quality of life measure for primary biliary cirrhosis," *Gut*, 2005;54:1622-1629.

Corpechot C., et al., "Biochemical response to ursodeoxycholic acid and long-term prognosis in primary biliary cirrhosis," *Hepatology*, 2008;48(3):871-877.

Carbone M., et al., "Sex and age are determinants of the clinical phenotype of primary biliary cirrhosis and response to ursodeoxycholic acid," *Gastroenterology*, 2013;144(3):560-569,e7.

Search report, ROC (Taiwan) Patent Application No. 108135837 (Translation), (2020).

* cited by examiner

TREATMENT OF PRIMARY BILIARY CHOLANGITIS AND PRIMARY SCLEROSING CHOLANGITIS WITH BARICITINIB

The present invention relates to the field of medicine. More particularly, the present invention relates to the treatment of primary biliary cholangitis (PBC) and primary sclerosing cholangitis (PSC).

Baricitinib is an approved medication that belongs to the pharmacological class of Janus kinase (JAK) inhibitors. Janus kinases are a family of four (4) protein tyrosine kinases (JAK1, JAK2, JAK3, and tyrosine kinase 2 [TYK2]) that play a role in cytokine signal transduction. Baricitinib demonstrates selectivity for, and inhibition of, JAK1 and JAK2 with lower potency towards inhibition of JAK3 or TYK2 (Fridman J S, et al., "Selective inhibition of JAK1 and JAK2 is efficacious in rodent models of arthritis: preclinical characterization of INCB028050," *J Immunol.* 2010; 184(9):5298-5307.) In isolated enzyme assays, baricitinib inhibited the activities of JAK1, JAK2, TYK2, and JAK3 with half-maximal inhibitory concentration values of 5.9, 5.7, 53, and >400 nM, respectively (See id.)

Janus kinases are enzymes that transduce intracellular signals from cell surface receptors for a number of cytokines and growth factors involved in hematopoiesis, inflammation, and immune function (e.g., interleukin [IL]-2, IL-6, IL-12, IL-15, IL-23, interferons, and granulocyte-macrophage colony-stimulating factor signal through the JAK family) (O'Shea et al., "The JAK-STAT pathway: impact on human disease and therapeutic intervention," *Annu Rev Med.* 2015; 66:311-28.) Within the intracellular signaling pathway, JAKs phosphorylate and activate signal transducers and activators of transcription (STATs), which activate gene expression within the cell. Baricitinib modulates these signaling pathways by partially inhibiting JAK1 and JAK2 enzymatic activity, reducing the phosphorylation and activation of STATs and reducing inflammation, cellular activation, and proliferation of key immune cells. (O'Shea et al., "JAKs and STATs in immunity, immunodeficiency, and cancer," *N Engl J Med. Review* 2013 Jan. 10; 368(2):161-70.)

PBC, formerly known as primary biliary cirrhosis, is a chronic and progressive cholestatic liver disease thought to be autoimmune in nature and is characterized by a T-lymphocyte-mediated attack on small intralobular bile ducts (Webb et al., "The immunogenetics of primary biliary cirrhosis: A comprehensive review," *J Autoimmun.* 2015; 64:42-52; Hirschfield et al., "The British Society of Gastroenterology/UK-PBC primary biliary cholangitis treatment and management guidelines," *Gut.* 2018 Mar. 28. [Epub ahead of print] (hereinafter "Hirschfield 2018").) When the intra-hepatic ducts in the liver are destroyed, bile builds up in the liver contributing to inflammation and fibrosis. (G. M. Hirschfield, M. E. Gershwin, "The immunobiology and pathophysiology of primary biliary cirrhosis," *Annu. Rev. Pathol. Mech. Dis.* 8 (1) (2013), pp. 303-330.) PBC is diagnosed frequently from routine liver biochemical tests obtained for other reasons (i.e., increased alkaline phosphatase (ALP)) while the patient is still asymptomatic or in early-stage disease when a patient seeks treatment for pruritus or fatigue (Hirschfield 2018). Untreated PBC typically progresses over several years to liver cirrhosis resulting in liver transplant or death.

Hirschfield 2018 outlines two proposed approaches for treating PBC. The first is to manage the production and disposal of bile acids that accumulate in the liver because of progressive destruction and impaired function of the bile ducts caused by chronic inflammation. (Hirschfield 2018). The second approach is to modify the autoimmune process that drives the disease. (Hirschfield 2018). To date, there has been no effective, approved method that treats PBC through this second approach (e.g., that modifies the autoimmune process causing the disease). The first approach to treating PBC generally involves using ursodeoxycholic acid ("UDCA"). UDCA was approved for treating PBC in 1997 and is now the standard of care for treating this disease (Hirschfield 2018). UDCA works by facilitating bile flow through the liver and protecting liver cells. Treatment with UDCA is recommended at diagnosis of PBC, regardless of disease stage.

Obeticholic acid (sold under the trademark OCALIVA®) was approved as an add-on to UDCA in patients with an inadequate response to UDCA or as monotherapy in patients who are intolerant to UDCA. (Nevens et al., POISE Study Group, "A Placebo-Controlled Trial of obeticholic Acid in Primary Biliary Cholangitis," *N Engl J Med.* 2016 Aug. 18; 375(7):631-43). However, neither UDCA nor OCALIVA® effectively addresses other major symptoms of PBC such as itch or fatigue. In fact, obeticholic acid (OCALIVA®) is associated with increased pruritus, and achieving and maintaining an effective dose is limited by this adverse effect (Nevens et al. 2016). Further, the use of obeticholic acid seems only to be effective in 55% or so of the patient population.

Thus, there are still segments of the patient population that do not respond to UDCA and are not adequately treated by obeticholic acid (either alone or in combination with UDCA). Still further, the itch and fatigue and pain associated with PBC are not treated by these current agents. Additionally, both UDCA and obeticholic acid operate by adjusting the production and disposal of bile acids in the liver, but do not treat the underlying condition—e.g., the autoimmune response that causes the T-lymphocyte-mediated attack on small intralobular bile ducts. For these and other reasons, a new treatment for PBC is needed. Accordingly, despite the advance in the field associated with the approval of obeticholic acid, it is clear that new treatments for PBC are needed.

PSC is different from PBC. PSC is a rare, chronic cholestatic liver disease characterized by intrahepatic or extrahepatic stricturing, or both, with bile duct fibrosis. PSC can involve inflammation and fibrosis of bile ducts and the liver as a result of impaired bile formation or flow and progressive liver dysfunction. (Jessica K Dyson, et al., *Lancet* 2018; 391: 2547-59.) The key diagnostic elements are cholestatic liver biochemistry and bile duct stricturing on cholangiography. Genetic and environmental factors are important in the cause of the disease, with the intestinal microbiome increasingly thought to play a pathogenetic role. Approximately 70% of patients have concurrent inflammatory bowel disease and patients require colonoscopic screening and surveillance (Dyson, et al., *Lancet* 2018; 391: 2547-59). PSC patients might present with cholestasis (elevation in ALP and γ-glutamyl transferase) after either screening in at-risk patients (typically with inflammatory bowel disease) or general health screening. Alternatively and particularly in patients with inflammatory bowel disease, PSC can be identified through the presence of compatible cholangiographic features even in patients with normal serum biochemistry. (Lunder A K, et al. *Gastroenterology* 2016; 151: 660-6.)

There is currently no known effective treatment for PSC; rather, patients suffering from PSC may ultimately require a liver transplant. UDCA has been tried as a treatment for PSC, but occlusion of major bile ducts in the liver still occurred in a majority of the patients. (Stiehl A, et al., "Development of dominant bile duct stenoses in patients with primary sclerosing cholangitis treated with ursodeoxycholic acid: outcome after endoscopic treatment," *J Hepatol.;* 36: 151-56, 2002.) Thus, there is medical unmet need for a new, approved and clinically effective treatment of PSC.

For at least the reasons provided herein, there exists an unmet need for an improved treatment of both PBC and PSC. Such treatment should address the autoimmune cause of PBC and PSC and, preferably, prevent or treat the autoimmune response that causes PSC or PBC in the liver. Additionally, such treatment for PBC should treat the non-responders to UDCA. Further, (especially for PBC), the treatment should address the itch (pruritus), fatigue and/or pain associated with these conditions. As with all therapeutic treatments, safety and toxicity remain a limitation, thus any improved treatments must not be attendant on unacceptable safety and toxicity profiles and provide a clinical benefit (especially for PSC, where there is no approved treatment). The present invention provides a therapeutic treatment for the treatment of PBC and/or PSC that overcomes one or more of the challenges recognized above.

In some embodiments, a method of treating a patient in need of treatment of one of PBC or PSC is provided comprising administering to said patient an amount of baricitinib, or a pharmaceutical formulation thereof. In some embodiments, the amount of baricitinib is administered orally. For example, the oral administration may comprise giving the patient a tablet or a pill that includes one or more excipients. In further embodiments, said pill comprises 4 mg of baricitinib, although other amounts of baricitinib may also be used. In some embodiments, the patient who is in need of treatment for PBC or PSC is a patient who does not respond to UDCA treatment.

Further embodiments comprise a method of treating a patient in need of treatment of one of PBC or PSC by administering to said patient an amount of baricitinib, or a pharmaceutical formulation thereof, wherein the patient's itch NRS score is assessed at Day 0 and then treatment with baricitinib is administered, and then the patient's itch NRS score is re-assessed. In some embodiments, after the itch NRS score is re-assessed, the patient's itch NRS score has decreased. In further embodiments, the itch NRS score is re-assessed during or after Week 12 of treatment with baricitinib. During some embodiments, this treatment involves administering baricitinib in a daily dose (at, for example, 4 mg or some other dose).

Additional embodiments comprise a method of treating a patient in need of treatment of one of PBC or PSC by administering to said patient an amount of baricitinib, or a pharmaceutical formulation thereof, wherein the patient's fatigue NRS score is assessed at Day 0 and then treatment with baricitinib is administered, and then the patient's fatigue NRS score is re-assessed. In some embodiments, after the fatigue NRS score is re-assessed, the patient's fatigue NRS score has decreased. In some of these embodiments, the fatigue NRS score is re-assessed during or after Week 12 of treatment with baricitinib. During some embodiments, this treatment involves administering baricitinib in a daily dose (at, for example, 4 mg or some other dose).

Embodiments may also comprise a method of treating a patient in need of treatment of one of PBC or PSC by administering to said patient an of baricitinib, or a pharmaceutical formulation thereof, wherein the patient's ALP is assessed at Day 0 and then treatment with baricitinib is administered, and then the patient's ALP is re-assessed. In some embodiments, after the ALP is re-assessed, the patient's ALP has decreased (such as, for example, at least a 15% decrease). In some of these embodiments, the ALP is re-assessed during or after Week 12 of treatment with baricitinib. During some embodiments, this treatment involves administering baricitinib in a daily dose (at, for example, 4 mg). In additional embodiments, after the ALP is re-assessed, the ALP is less than 1.67*ULN (Upper Limit of Normal). Further embodiments are after the ALP is re-assessed, the patient's bilirubin is less than ULN.

According to other embodiments, an amount of baricitinib, or a pharmaceutical formulation thereof is provided for use in the manufacture of a medicament for the treatment of at least one of PBC and PSC. In many of these embodiments, the amount of the baricitinib comprises a 4 mg pill.

Furthermore, the present invention provides baricitinib, or a pharmaceutical formulation comprising baricitinib, for use in treating Primary Biliary Cholangitis. The present invention also provides baricitinib, or a pharmaceutical formulation comprising baricitinib, for use in treating Primary Sclerosing Cholangitis. In some embodiments, the baricitinib, or a pharmaceutical formulation comprising baricitinib, for use is in the form of a pill that includes one or more excipients. In other embodiments, the baricitinib, or a pharmaceutical formulation comprising baricitinib, for use is to be administered to a patient who has had an inadequate response to or is intolerant to ursodeoxycholic acid. Additional embodiments have the baricitinib, or a pharmaceutical formulation comprising baricitinib, for use wherein the patient's itch NRS score is assessed at Day 0 and re-assessed following administration of baricitinib. Yet further embodiment have the baricitinib, or a pharmaceutical formulation comprising baricitinib, for use wherein the patient's fatigue NRS score is assessed at Day 0 and re-assessed following administration of baricitinib. Additionally, the baricitinib, or a pharmaceutical formulation comprising baricitinib, for use will have the patient's ALP score, NRS fatigue score, or NRS itch score is assessed at Day 0 and reassessed following administration of baricitinib. Additionally, the baricitinib, or a pharmaceutical formulation comprising baricitinib, for use will have the reassessment of ALP occur during or after Week 12. The baricitinib may be administered daily, in for example, a 4 mg dose.

The present embodiments relate to the use of baricitinib in the manufacture of a medicament for the treatment of PBC. The present embodiments also relate to the use of baricitinib in the manufacture of a medicament for the treatment of PSC. This use may have the baricitinib in the form of a pill that includes one or more excipients. This use may also have the baricitinib to be administered to a patient who has had an inadequate response to or is intolerant to ursodeoxycholic acid. The use may also be such that the patient's itch NRS score is assessed at Day 0 and re-assessed following administration of baricitinib. The use may further be such that the patient's fatigue NRS score is assessed at Day 0 and re-assessed following administration of baricitinib. The use may also be such that the patient's ALP score is assessed at Day 0 and reassessed following administration of baricitinib. The use may further be such that the reassessment occurs during or after Week 12. The use may further be such that the baricitinib is administered daily, such as, for example, in a 4 mg daily dose.

Baricitinib is a Janus kinase (JAK) inhibitor (and more specifically a selective JAK 1 and JAK 2 inhibitor) with the chemical name {1-(ethylsulfonyl)-3-[4-(7H-pyrrolo[2,3-d]

pyrimidin-4-yl)-1H-pyrazol-1-yl]azetidin-3-yl}acetonitrile. Baricitinib has the following structural formula:

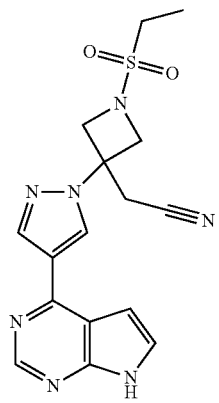 [SMILES: CCS(=O)(=O)N1CC(CC#N)(n2cc(-c3ncnc4[nH]ccc34)cn2)C1]

Additional information about baricitinib including methods of making the compound may be found in U.S. Pat. Nos. 8,158,616 and 8,420,629. Additional methods for making baricitinib are found in U.S. Patent Application Publication No. 2018/0134713.

Baricitinib is a known medicine that is approved in the United States and Europe (and other countries) for the treatment of rheumatoid arthritis and is commercially available under the trademark OLUMIANT®. In some jurisdictions, OLUMIANT® is available in pill form, wherein the pill includes a designated amount of baricitinib and the following excipients: croscarmellose sodium, magnesium stearate, mannitol, microcrystalline cellulose, ferric oxide, lecithin (soya), polyethylene glycol, polyvinyl alcohol, talc and titanium dioxide. In preferred embodiments of the present invention, the amount of baricitinib that used to treat the patient is administered by giving the patient one or more pills of OLUMIANT®. Of course, other dosages forms, pharmaceutical compositions of baricitinib, etc. may also be used. A Phase I study for baricitinib with patients who have liver disease has been conducted.

As referred to herein and as generally known in the art, the term "dose" refers to an amount of baricitinib that is administered to a subject. A "dose regimen" or "dosage regimen" as generally known in the field and as may be referred to interchangeably herein includes a treatment schedule for administering a set (i.e., series or sequence) of doses to be administered to a patient over a period of time.

The present invention includes a dose regimen the PBS or PBC treatments of the present invention. Specifically, prior to receiving treatment with baricitinib, (which is referred to as "Day 0") the patient's condition is assessed. This assessment may involve determining one or more of the following: the patient's NRS itch score, the patient's ALP, the patient's bilirubin measurement and/or the patient's fatigue NRS score. In some embodiments, all of these measurements (and other measurements) may be taken. It should be noted that Day 0 refers to measuring before actually starting to receive baricitinib treatment. Such measurements can be done the day before starting to receive baricitinib, the week before, etc., depending upon the particular embodiment. In some embodiments, Day 0 may be up to 6 weeks (42 days) prior to beginning therapy. In other embodiments, Day 0 can be the first day where the patient receives treatment with baricitinib.

In some embodiments, at Day 1, the patient will begin to receive treatment with baricitinib. According to some embodiments, this administration of baricitinib may occur daily (or at some other specified dosing time period) and be at the dose of 4 mg of baricitinib (such as, for example by directing the patient to administer a 4 mg pill of baricitinib). In some of the presently preferred embodiments, each day throughout a 12-week period, the patient is directed to take a daily dose of baricitinib. The amount of baricitinib may vary. In some embodiments, the patient takes 4 mg per day while in other embodiments, different doses of baricitinib (e.g., 2 mg, 8 mg, etc.) are given as determined by the patient and/or his or her physician.

Then, at some point in the future (e.g., after Day 1), the patient's condition is re-assessed, which involves by determining one or more of the measurements that were taken at Day 0. In some of the presently preferred embodiments, this re-assessment occurs during or after the patient has received baricitinib treatment for 12 weeks. In other embodiments, the re-assessment will occur on or after a different time interval, such as for example, during or after Week 24, Week 36, Week 52, etc. In some embodiments, when the patient is re-assessed, the patient's itch NRS score has decreased. In other embodiments, when the patient is re-assessed, the patient's fatigue NRS score has decreased. Such decrease of the fatigue NRS score and/or the itch NRS score may be statistically significant. In further embodiments, when the patient is re-assessed, the patient's ALP has decreased, such as, for example, by 10%, 15% 20%. In some such embodiments, the patient's ALP score has decreased to a value that is less than 1.67*ULN. Further embodiments are where, at re-assessment, the patient's bilirubin has decreased. Such lowering of the patient's bilirubin may be such that the measure of the patient's bilirubin is less than ULN. (According to some embodiments, the patient's ALP levels may be assessed and/or re-assessed in a manner outlined in Nevens et al., POISE Study Group, "A Placebo-Controlled Trial of Obeticholic Acid in Primary Biliary Cholangitis," *N Engl J Med.* 2016 Aug. 18; 375(7):631-43.)

In some embodiments, before the patient receives treatment, his or her ALP value may be 2.5, three times that of normal, four times that of normal, six times that of normal, etc. However, after therapy of baricitinib, in the manner outlined herein, the patient's ALP may decrease to a value that is less than or equal to 1.67*ULN. In fact, baricitinib phase 3 trials showed that the patient's ALP decreased after treatment. (See EMA Committee for Medicinal Products for Human Use "Assessment Report" for Olumiant.)

When the patient is re-assessed (and the various measurements are taken), the patient's dose and/or treatment may be adjusted. For example, the amount of baricitinib that the patient is taking may be adjusted (such as to 2 mg or to a higher amount daily). Likewise, the frequency of the drug administration (e.g., daily) may be adjusted so that the patient is taking the medicine more frequently or less frequently. In other embodiments, the patient may remain on the same treatment dose and/or schedule. In other embodiments, the patient may be taken off the drug after the re-assessment.

As should be understood, "Day 1" as used herein refers to the day on which the first dose of baricitinib is administered. As referred to herein, "Week" refers to a 7 day calendar. Thus, if Day 1 is on a Monday, then that week (e.g., Monday-Sunday) constitutes "Week 1" and "Week 2" starts on the following Monday.

The itch NRS score, as used herein, refers to a score that is patient-assessed. This score is an eleven-point horizontal scale anchored at zero (0) and ten (10), with zero representing "no itch" and 10 representing "worst itch imaginable." Overall severity of a patient's itching is indicated by selecting the number that describes the worst level of itching in the past 7 days. The patient will assess their score weekly and, as noted above, after a period of time (such as 12 weeks, for example) the overall itch NRS score—as compared to the initial itch NRS score will go down. In some embodiments, as the patient is receiving treatment with baricitinib for their itch, in addition to the baricitinib treatment, the patient may also maintain their usual medication regimen for PBC, including background therapy consisting of corticosteroids, and/or anti-itch therapies.

The fatigue NRS score, as used herein, refers to a score that patient-administered and patient-assessed. This score is an eleven-point horizontal scale anchored at zero (0) and ten (10), with 0 representing "no fatigue" and 10 representing "as bad as you can imagine." Overall severity of a patient's fatigue is indicated by selecting the number that describes the worst level of fatigue during the past 7 days. The patient will assess their score weekly and, as noted above, after a period of time (such as 12 weeks, for example) the overall fatigue NRS score—as compared to the initial fatigue NRS score will go down.

In addition to determining itch or fatigue NRS score at specified time points, alternative embodiments may be based upon other known pathophysiological endpoints. This includes testing, assessing and re-assessing the patient's FACIT-F score. The FACIT-F measures an individual's self-reported level of fatigue during their usual daily activities over the past 7 days (or over some other 7 day period (or some other period of time)). The scale is composed of 13 items measured on a 4-point scale (4=very much to 0=not at all). The total score ranges from 0 to 52, and higher scores representing less fatigue. A score of less than 30 indicates severe fatigue (For additional information on this FACIT-F survey and its scoring, see Webster K. et al., "The Functional Assessment of Chronic Illness Therapy (FACIT) measurement system: properties, applications, and interpretation," *Health Qual Life Outcomes* 2003; 1:79.) Likewise, the patient's "PBC-40" survey score may also be assessed and re-assessed. The PBC-40 is a disease-specific, 40-item, patient-reported survey containing 6 domains: overall symptoms, itch, fatigue, cognition, social, and emotional. Response options for overall symptoms, itch, fatigue, and cognition are on a 5-point scale: "Never," "Rarely," "Sometimes," "Most of the time," and "Always." Response options are also on a 5-point scale for social and emotional: "Not at all," "A little," "Somewhat," "Quite a bit," and "Very much." Items are scored from 1 to 5 and the individual item scores are summed to give a total domain score where high scores represent high impact of PBC on quality of life (For additional information on this PBC-40 survey and its scoring, see Jacoby A., et al., "Development, validation, and evaluation of the PBC-40, a disease specific health related quality of life measure for primary biliary cirrhosis," *Gut*, 2005; 54:1622-1629.) Other information may also be assessed and re-assessed that is provided by the patient as determined by the doctor, the clinician and/or the patient, including the patient's pain level or discomfort level associated with PSC or PBC and whether or not treatment with baricitinib is reducing/alleviating the pain.

In some of the present embodiments, the patient that is treated with baricitinib has been receiving UDCA prior to receiving baricitinib. In some embodiments, the patient will have been receiving UCDA for 52 weeks or more prior to beginning therapy on baricitinib. In other embodiments, the patient will have received UDCA for at least 12 weeks prior to beginning therapy on baricitinib. In further embodiments, the patient who receives baricitinib therapy for PBC or PSC is a patient that has had an inadequate response to or is intolerant to UDCA. To determine whether a patient has an inadequate response to or is intolerant to UDCA, the patient is assessed and determined to have a lack of improvement in liver biochemistry, as outlined by the methods taught in the following two (2) articles:

Corpechot C., et al., "Biochemical response to ursodeoxycholic acid and long-term prognosis in primary biliary cirrhosis," *Hepatology*, 2008; 48(3):871-877; and Carbone M., et al., "Sex and age are determinants of the clinical phenotype of primary biliary cirrhosis and response to ursodeoxycholic acid," *Gastroenterology*, 2013; 144(3):560-569.e7.

As referred to herein, the terms "individual," "subject," and "patient," used interchangeably herein, refer to a human. In a certain embodiment, the subject is further characterized with a disease, disorder, or condition that would benefit from a decreased bioactivity of JAK 1 or JAK 2.

As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of baricitinib for treatment of PBC or PSC and includes: (a) inhibiting further progression of PBC or PSC, i.e., arresting its development; and (b) relieving PBC or PSC, i.e., causing regression of PBC or PSC or alleviating symptoms or complications thereof. Treatment also includes preventing the onset of PBC or PSC, preventing the likelihood of the onset of PBC or PSC, and/or reducing the severity of PBC or PSC. Treatment also includes preventing an episode or an "attack" of PBC or PSC and/or reducing the likelihood that such an "attack" occurs.

In further embodiments, the patient that receives the baricitinib (e.g., the patient that has PBC and/or PSC) does not have rheumatoid arthritis, lupus or atopic dermatitis.

It should also be noted that the label for baricitinib in the United States indicates the following:

Liver Enzyme Elevations—Treatment with OLUMIANT was associated with increased incidence of liver enzyme elevation compared to placebo. Increases to greater than or equal to 5× and greater than or equal to 10× upper limit of normal (ULN) were observed for both ALT and AST in patients in OLUMIANT clinical trials. Evaluate at baseline and thereafter according to routine patient management. Prompt investigation of the cause of liver enzyme elevation is recommended to identify potential cases of drug-induced liver injury. If increases in ALT or AST are observed and drug-induced liver injury is suspected, interrupt OLUMIANT until this diagnosis is excluded [see Adverse Reactions (6.1)].

Yet, despite this elevation of liver enzymes, baricitinib may be an effective treatment for PBC and/or PSC.

In Vivo Study

Patients are divided into treatment groups consisting of double-blinded placebo and baricitinib therapy groups. Baricitinib therapy groups are administered an amount of baricitinib (for example, a 4 mg pill or tablet in the manner outlined herein), whereas the placebo group are administered a pill that has only placebo (e.g., a 4 mg pill or tablet of placebo).

There are generally 3 periods in the study, e.g., a "screening period," a "treatment period" and a "follow-up period". All patients go through each of these periods.

In the screening period, which occurs before treatment begins, the patients are assessed for one or more of the following: bilirubin level, ALP, itch NRS score, fatigue NRS score and/or other measurements. This screening period may constitute "Day 0". These assessments are done prior to the patient receiving treatment.

During the treatment period, the patients are given either placebo or baricitinib (depending upon which group of the study they are in). In some situations, randomized patients will take the first dose of investigational product at the clinic and pharmacokinetic (PK) samples will be drawn 15 minutes and 1 hour post dose. Baricitinib may be daily for 12 weeks. Clinical assessments and laboratory samples, including additional PK sampling, is obtained at scheduled visits during the treatment period. During the treatment period, in addition to randomized treatment, patients will also maintain their usual medication regimen for PBC, including background therapy consisting of corticosteroids, and/or anti-itch therapies. Re-assessment of the patient's measurements (such as those measurements above) may occur at any time during the treatment period.

After the treatment period (which may last, for example, 12 weeks), the patient enters the follow-up period. During this period, the patient's measurements are re-assessed (or further re-assessed).

We claim:

1. A method of treating a patient in need of treatment for Primary Biliary Cholangitis (PBC) comprising administering to said patient an amount of baricitinib, or a pharmaceutical formulation thereof.

2. A method of treating a patient in need of treatment for Primary Sclerosing Cholangitis (PSC) comprising administering to said patient an amount of baricitinib, or a pharmaceutical formulation thereof.

3. The method of claim 1, wherein the amount of baricitinib is administered orally.

4. The method of claim 1, wherein the patient has previously had an inadequate response to or is intolerant to ursodeoxycholic acid.

5. The method of claim 1, further comprising:
assessing the patient's itch NRS score at Day 0; and
re-assessing the patient's itch NRS score following said step of administering baricitinib.

6. The method of claim 1, further comprising:
assessing the patient's fatigue NRS score at Day 0; and
re-assessing the patient's fatigue NRS score following said step of administering baricitinib.

7. The method of claim 1, further comprising:
assessing the patient's ALP at Day 0; and
re-assessing the patient's ALP following said step of administering baricitinib.

8. The method of claim 5, wherein the step of re-assessing the patient's itch NRS score occurs during or after Week 12.

9. The method of claim 1, wherein administering baricitinib comprises administering baricitinib to the patient in a daily dose of 4 mg.

10. The method of claim 2, wherein the amount of baricitinib is administered orally.

11. The method of claim 2, wherein the patient has previously had an inadequate response to or is intolerant to ursodeoxycholic acid.

12. The method claim 2, further comprising:
assessing the patient's itch NRS score at Day 0; and
re-assessing the patient's itch NRS score following said step of administering baricitinib.

13. The method of claim 2, further comprising:
assessing the patient's fatigue NRS score at Day 0; and
re-assessing the patient's fatigue NRS score following said step of administering baricitinib.

14. The method of claim 2, further comprising:
assessing the patient's ALP at Day 0; and
re-assessing the patient's ALP following said step of administering baricitinib.

15. The method of claim 12, wherein the step of re-assessing the patient's itch NRS score occurs during or after Week 12.

16. The method of claim 2, wherein administering baricitinib comprises administering baricitinib to the patient in a daily dose.

17. The method of claim 6, wherein the step of re-assessing the patient's fatigue NRS score occurs during or after Week 12.

18. The method of claim 7, wherein the step of re-assessing the patient's ALP occurs during or after Week 12.

19. The method of claim 13, wherein the step of re-assessing the patient's fatigue NRS occurs during or after Week 12.

20. The method of claim 14, wherein the step of re-assessing the patient's ALP occurs during or after Week 12.

* * * * *

UNITED STATES PATENT AND TRADEMARK OFFICE
CERTIFICATE OF CORRECTION

PATENT NO. : 11,197,860 B2
APPLICATION NO. : 16/598241
DATED : December 14, 2021
INVENTOR(S) : Patrick L. McCollam et al.

It is certified that error appears in the above-identified patent and that said Letters Patent is hereby corrected as shown below:

On the Title Page

| Column | Line | |
|---|---|---|
| 2<br>Item (56)<br>(Other Publications) | 1 | Delete "o f" and insert -- of --, therefor. |
| 2<br>Item (56)<br>(Other Publications) | 34 | Delete "Bihary" and insert -- Biliary --, therefor. |
| 2<br>Item (56)<br>(Other Publications) | 36 | Delete ""Primaiy" and insert -- "Primary --, therefor. |
| 2<br>Item (56)<br>(Other Publications) | 43 | Delete "inpatients" and insert -- in patients --, therefor. |

In the Claims

| Column | Line | |
|---|---|---|
| 10 | 18 | In Claim 12, delete "method" and insert -- method of --, therefor. |

Signed and Sealed this
First Day of August, 2023

Katherine Kelly Vidal
*Director of the United States Patent and Trademark Office*